US00PP35724P2

(12) United States Plant Patent
Clark

(10) Patent No.: US PP35,724 P2
(45) Date of Patent: Apr. 2, 2024

(54) ***COLEUS* PLANT NAMED 'UF21-9-4'**

(50) Latin Name: *Coleus scutellarioides*
Varietal Denomination: UF21-9-4

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 18/445,290

(22) Filed: Jun. 20, 2023

(51) Int. Cl.
*A01H 5/12* (2018.01)
*A01H 6/50* (2018.01)

(52) U.S. Cl.
USPC ..... Plt./469

(58) Field of Classification Search
USPC ..... Plt./469
See application file for complete search history.

(56) References Cited

U.S. PATENT DOCUMENTS

PP29,820 P3 11/2018 Clark et al.

OTHER PUBLICATIONS https://emea.dummenorange.com/app/en/products/netherlands/coleus/down-town-greenville/PAT_71071- Retrieved from the Internet on Oct. 10, 2023 (4 pages total).* https://hort.ifas.ufl.edu/uf-coleus-breeding-program/our-cultivars/. Retrieved from the Internet on Oct. 10, 2023 (1 page total).*

* cited by examiner

*Primary Examiner* — Susan McCormick Ewoldt
(74) *Attorney, Agent, or Firm* — Koenig IP Works, PLLC; Katherine Koenig

(57) ABSTRACT

A new and distinct cultivar of *Coleus* (*Coleus scutellarioides*) plant named 'UF21-9-4' having a combination of desirable traits that makes it well-suited for use as a colorful annual plant in the summer landscape. 'UF21-9-4' has consistent foliage color patterning and fast growth rate and vigor in the greenhouse and landscape. 'UF21-9-4' has lance-shaped foliage that is predominantly yellowish green with consistent reddish brown centers and light yellow green spots. 'UF21-9-4' is exceptional because it maintains these contrasting colors and patterns in both sun and shade. 'UF21-9-4' is compact and upright in growth habit, but it is highly branched and spreading in form, growing wider than it does tall.

3 Drawing Sheets

Genus and species: *Coleus scutellarioides*.
Cultivar denomination: 'UF21-9-4'.

CROSS-REFERENCE TO RELATED APPLCIATIONS

N/A.

ACKNOWLEDGEMENT OF FEDERAL RESEARCH SUPPORT

N/A.

BACKGROUND OF THE NEW CULTIVAR

The invention relates to a new and distinct cultivar of *Coleus* plant named 'UF21-9-4'. The new cultivar 'UF21-9-4' originated from an open pollination conducted in May-November 2020 in Citra, Florida, between the female *Coleus* plant 'UF20-19-8' (unpatented) and an unknown male *Coleus* plant. A single seedling was chosen in May 2021 for further asexual propagation in Gainesville, Florida.

The new cultivar 'UF21-9-4' has been reproduced asexually for over 18 months through vegetative meristem tip cuttings and has been found to retain its distinctive characteristics through successive asexual propagations. 'UF21-9-4' was first propagated asexually by vegetative meristem tip cuttings in May 2021 in Gainesville, Florida, and has remained true-to-type since that time.

Plant Breeder's Rights for the new cultivar 'UF21-9-4' have not been applied for, and 'UF21-9-4' has not been made publicly available more than one year prior to the filing date of this application.

SUMMARY OF THE INVENTION

The new cultivar 'UF21-9-4' has not been observed under all possible environmental conditions. The phenotype of the new cultivar may vary with variations in environment and cultural practices such as temperature, light intensity, fertilization, irrigation, and application of plant growth regulators without any change in genotype.

The new cultivar 'UF21-9-4' was selected for its novel combination of foliage shape and color patterning. It was also selected for its fast growth rate and vigor in the greenhouse and landscape. 'UF21-9-4' has foliage that is predominantly colored yellowish green with reddish brown color in the center of the leaf around the midveins. 'UF21-9-4' is novel due to its regular distribution of light yellow green spots across both predominant colors of the leaf surface. Normally this color combination changes in either full sun (predominantly dark brick red) or full shade (predominantly darker green), with the consistent loss of the distinctive reddish brown leaf center. 'UF21-9-4' is exceptional because it maintains consistent colors in both sun and shade, and the yellow spots remain stable in both conditions.

The following are the most outstanding and distinguishing characteristics of 'UF21-9-4' when grown under normal horticultural practices in Gainesville, Florida: (1) 'UF21-9-4' has the combination of compact, upright habit and spreading growth form, excellent heat tolerance, and consistent multi-colored leaves that are significantly different than other *Coleus* plants; (2) it has superior stability in foliage color in both sun and shade conditions, and it has a vigorous growth habit with excellent lateral branching, making it suitable for propagators and producers; and (3) 'UF21-9-4' has been observed to have long-season performance in landscape trials in Gainesville, Florida.

When compared to the female parent 'UF20-19-8', the new cultivar 'UF21-9-4' has larger lance-shaped leaves that are longer than they are wide. Leaves of 'UF21-9-4' are predominantly colored yellowish green with reddish brown centers and light yellow green spots. In contrast, 'UF20-19-8' has smaller lance-shaped leaves that are colored deep crimson with chartreuse highlights at the leaf margins. Additionally, 'UF21-9-4' has a vigorous, compact, and upright growth habit with a spreading form that is well-branched, whereas 'UF20-19-8' is less vigorous, and more upright in habit with less lateral branching and a less spreading form.

DESCRIPTION OF THE FIGURES

This new *Coleus* cultivar 'UF21-9-4' is illustrated by the accompanying photographs, which show the plant's form and foliage. The colors shown are as true as can be reasonably obtained by conventional photographic procedures.

FIG. 2 shows the growth habit, form, and foliage of the new *Coleus* cultivar; and FIG. 3 shows a close-up view of the foliage of the new *Coleus* cultivar.

DETAILED BOTANICAL DESCRIPTION OF THE CULTIVAR

Figure 1:
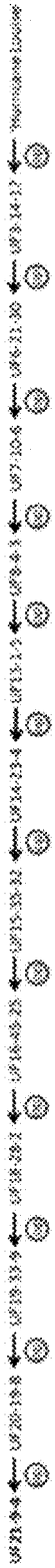
FIG. 1 shows the pedigree of the new *Coleus* cultivar 'UF21-9-4' as is shown and described herein.
Figure 2:
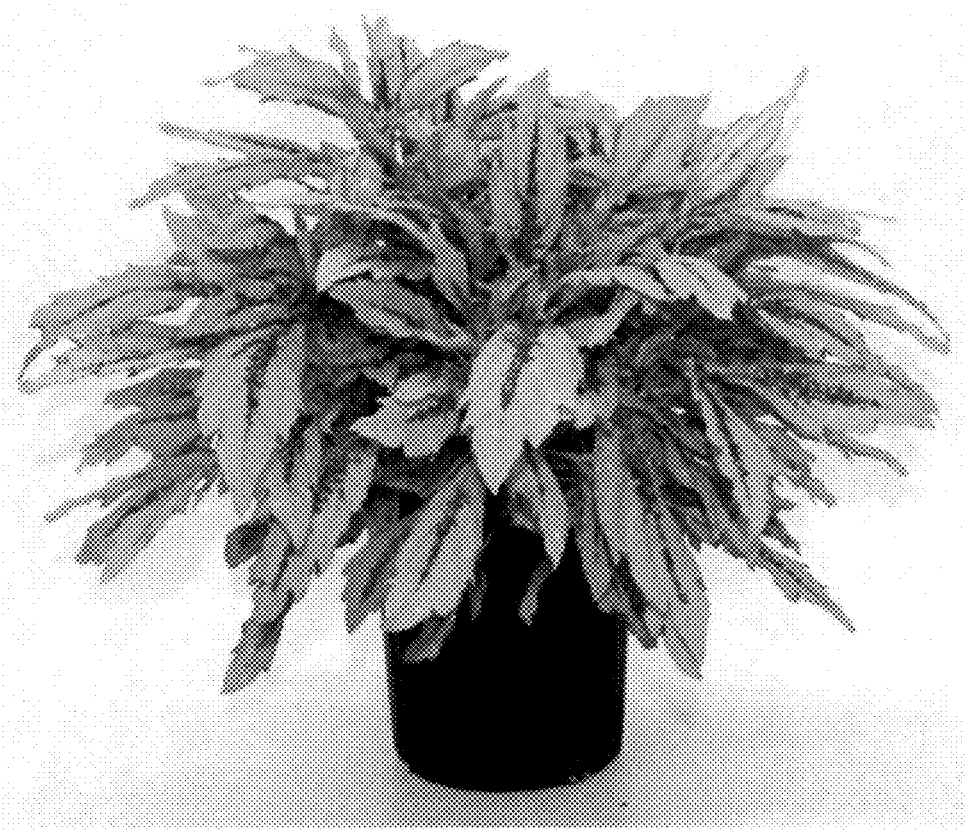
FIGS. 2 and 3 were taken from plants grown eleven weeks from unrooted cuttings in September-December 2022 in a glass-covered greenhouse in Gainesville, Florida.
Figure 3:
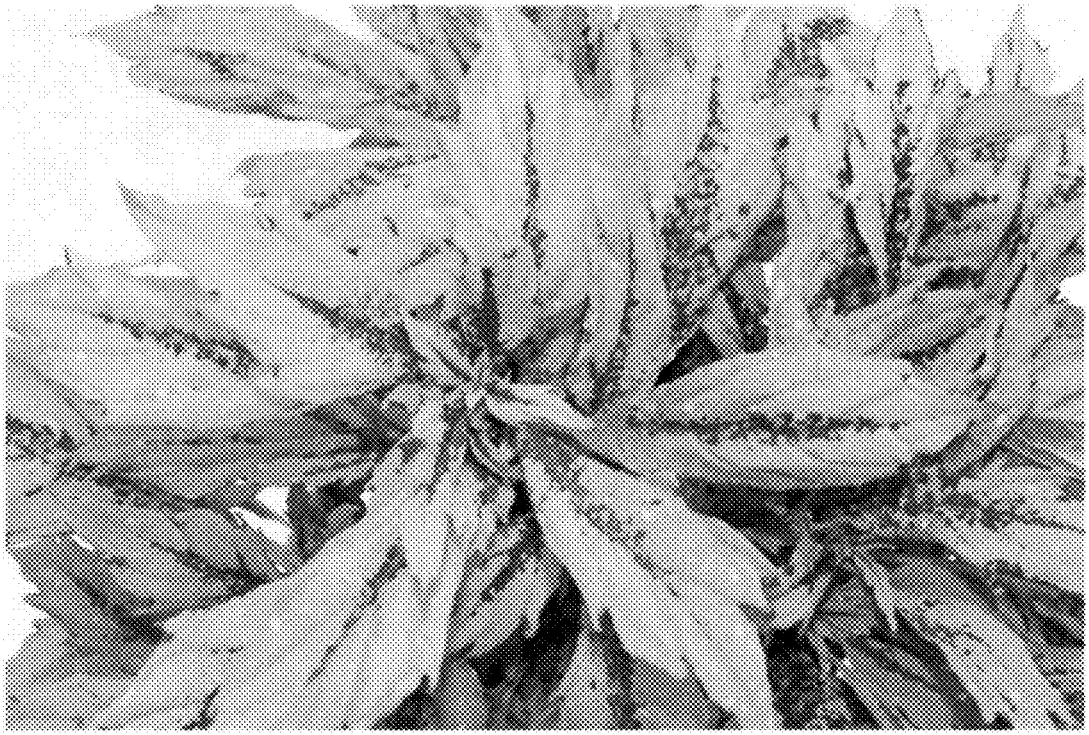

Foliage color was determined under full sun conditions in the middle of the day in a glass-covered greenhouse. Color references are to The R.H.S. Colour Chart of The Royal Horticultural Society of London (R.H.S.), 2007 5th Edition. *Coleus* leaves are rarely one solid color, but encompass hues, shades and tints, and color patterns differ from one genotype to another due to varying levels of variegation. The following detailed description of 'UF21-9-4' was obtained using eleven-week-old plants grown from unrooted cuttings in September-December 2022 in a glass-covered greenhouse in Gainesville, Florida. The plants were propagated in mist for ten days after cuttings were stuck, pinched, then grown in one-gallon pots for approximately nine and a half additional weeks.

Botanical Description

Botanical classification:
- *Family*.—Lamiaceae.
- *Botanical name*.—*Coleus scutellarioides*.
- *Common name*.—*Coleus*.
- *Cultivar name*.—'UF21-9-4'.

Parentage:
- *Female or seed parent*.—'UF20-19-8'.
- *Male or pollen parent*.—Unknown.

Plant description:
- *Form*.—Spreading.
- *Habit*.—Compact, upright.
- *Height* (*from top of soil*).—20-25 cm.
- *Width* (*horizontal plant diameter*).—50-55 cm.

Propagation:
- *Type cuttings*.—Vegetative meristems having at least 1 node.
- *Time to initiate roots*.—3-4 days.
- *Time to produce a rooted cutting*.—7-10 days.
- *Root habit*.—Fibrous.
- *Root description*.—Callus forms in 2-3 days, roots initiate in 3-4 days and become a highly branched cutting in 7-10 days.

Branches:
- *Quantity per plant*.—Approximately 9.
- *Branch color*.—RHS 143C (yellow green) and RHS 187A (dark red).
- *Texture*.—Smooth.
- *Pubescence*.—Not present.
- *Stem description*.—Square-shaped stem.
- *Branch diameter*.—0.7-0.8 cm at the base of an 18-cm-long branch.
- *Branch length*.—15-20 cm.
- *Internode length*.—2.5-3.0 cm measured at mid-branch.
- *Anthocyanin*.—Not present.

Leaves:
- *Quantity of leaves per branch*.—18-20.
- *Arrangement*.—Opposite.
- *Fragrance*.—Not fragrant.
- *Shape*.—Lanceolate.
- *Length*.—12-13 cm.
- *Width*.—5-6 cm.
- *Apex*.—Broadly Acute.
- *Base*.—Attenuate.
- *Margin*.—Lobed.
- *Leaf texture*.—Adaxial (top): Pulverulent. Abaxial (bottom): Smooth.
- *Venation color*.—Upper surface: RHS 187B (dark red). Lower surface: RHS 144B (yellow green).
- *Venation pattern* (*both upper and lower surfaces*).—Reticulate.
- *Color, immature leaf*.—Upper surface: Major color: RHS N144A (yellowish green). Center & mid-veins: RHS 175A (reddish orange). Spots: RHS 145D (light yellow green). Lower surface: Major color: RHS 144B (yellow green). Spots: RHS 145D (light yellow green).
- *Color, mature leaf*.—Upper surface: Major color: RHS N144A (yellowish green). Center & mid-veins: RHS 175A Reddish brown). Spots: RHS 145D (light yellow green). Lower surface: Major color: RHS 144B (yellow green). Spots: RHS 145D (light yellow green).
- *Petiole length*.—Approximately 6 cm.
- *Petiole diameter*.—0.2-0.3 cm.
- *Petiole color*.—RHS 144B (yellow green).
- *Petiole texture*.—Smooth, no pubescence.

Flowers and seeds: Flowers and seeds have not been observed to date during formal trials in Gainesville, Florida.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Florida have been long-tailed or citrus mealybugs (*Pseudococcus* spp.), which occur on older stock plant material held in the greenhouse for over 3-4 months. Impatiens Necrotic Spot Virus (Bunyaviridae) has also been observed in plants confined in greenhouses with mixed crops (peppers) infected with Western flower thrips (*Frankliniella occidentalis*). The most common pathogen of this species in the U.S. is downy mildew (*Perononspora lamii*). This pathogen has been observed in stock materials grown closely together in cooler growing seasons.

Winter hardiness: Not winter hardy, grown as a summer annual in USDA zones below 7.

Heat and drought tolerance: Heat tolerance when grown in moist and well-drained soil. Not drought tolerant.

Comparison with Known Cultivars

When compared to the *Coleus* cultivar 'UF14-24-1' (U.S. Plant Pat. No. 29,820, commercial name Salsa Verde), the new *Coleus* cultivar 'UF21-9-4' has a distinct center-leaf coloration of reddish brown surrounded by yellow green on the upper surface of mature leaves. In contrast, 'UF14-24-1' has an entirely yellowish green leaf coloration with no distinct center coloration on the upper surface of mature leaves.

What is claimed is:

1. A new and distinct *Coleus scutellarioides* plant named 'UF21-9-4' as shown and described herein.

* * * * *